United States Patent [19]

Asato

[11] Patent Number: 4,477,680

[45] Date of Patent: Oct. 16, 1984

[54] 3-AMINO-4-HYDROXY(OR ALKOXY)PHENETHANOLAMINE DERIVATIVES AND PHARMACOLOGICALLY ACCEPTABLE ACID ADDITION SALTS THEREOF FOR INCREASING THE GROWTH RATE AND/OR IMPROVING THE LEAN MEAT TO FAT RATIO OF WARM-BLOODED ANIMALS

[75] Inventor: Goro Asato, Titusville, N.J.

[73] Assignee: American Cyanamid Company, Stamford, Conn.

[21] Appl. No.: 439,495

[22] Filed: Nov. 5, 1982

Related U.S. Application Data

[63] Continuation-in-part of Ser. No. 326,878, Dec. 2, 1981, Pat. No. 4,404,224.

[30] Foreign Application Priority Data

Oct. 6, 1982 [GB] United Kingdom ................. 8228528

[51] Int. Cl.³ ..................... C07C 143/74; A61K 31/18
[52] U.S. Cl. ..................... 564/82; 424/309; 424/311; 424/321; 424/322; 424/324; 424/330
[58] Field of Search ......................... 564/82

[56] References Cited

U.S. PATENT DOCUMENTS

| | | | |
|---|---|---|---|
| 3,341,584 | 9/1967 | Lareen et al. | 564/99 X |
| 3,574,741 | 4/1971 | Gould et al. | 564/82 X |
| 3,660,487 | 5/1972 | Lareen et al. | 564/99 X |
| 3,701,808 | 10/1972 | Hartley et al. | 564/99 |
| 3,801,631 | 4/1974 | Comer et al. | 564/99 X |

Primary Examiner—Thomas A. Waltz
Attorney, Agent, or Firm—Estelle J. Tsevdos; Alphonse R. Noë

[57] ABSTRACT

A method for increasing the growth rate and/or improving the lean meat to fat ratio in farm and domestic animals. An effective amount of a 3-amino-4-hydroxy-(or alkoxy)phenethanolamine derivative, pharmacologically-acceptable acid addition or metal salt thereof is administered either orally or parenterally to animals. Novel 3-amino-4-hydroxy(or alkoxy)phenethanolamine derivatives are also described.

3 Claims, No Drawings

3-AMINO-4-HYDROXY(OR ALKOXY)PHENETHANOLAMINE DERIVATIVES AND PHARMACOLOGICALLY ACCEPTABLE ACID ADDITION SALTS THEREOF FOR INCREASING THE GROWTH RATE AND/OR IMPROVING THE LEAN MEAT TO FAT RATIO OF WARM-BLOODED ANIMALS

This is a continuation-in-part of co-pending application Ser. No. 326,878, filed Dec. 2, 1981, now U.S. Pat. No. 4,404,224.

The invention herein described relates to a method for increasing the growth rate, enhancing the lean meat deposition and/or improving the lean meat to fat ratio in warm-blooded animals, particularly farm and domestic animals (i.e., swine, poultry, cattle, sheep, goats, rabbits, cats, dogs, etc.). The method involves either oral or parenteral administration of various 3-amino-4-hydroxy(or alkoxy)phenethanolamine derivatives, including novel derivatives presently revealed.

By way of background, sulfonanilide derivatives, their acid addition and metal salts are disclosed in U.S. Pat. Nos. 3,341,581 and 3,801,631. These patents reveal that the above-mentioned compounds are useful as adrenergic neurotransmitters, vasopressors, vasodepressors, analgesics, bronchodilators, α-receptor stimulants, β-receptor stimulants, α-receptor blocking agents, β-receptor blocking agents, papaverine-like smooth muscle depressants and anti-inflammatory agents.

In addition to the above-said sulfonanilide derivatives, related 3-amino-4-hydroxyphenethanolamine derivatives are described with similar pharmacological activities in the following publications: Belgium Pat. Nos. 784,105; 762,504 and 765,988; U.S. Pat. Nos. 3,763,232; 3,917,847 and 3,711,545; *Journal of Medicinal Chemistry*, 10, 762–472 (1967), ibid., 17, 49–57 (1974) and ibid., 19, 626–633 (1976).

In recent years, the cost of raising meat animals has increased markedly in response to economic fluctuations in the areas of energy resources, ancillary products, and consumer markets. The necessity of providing adequate meat protein supplies to an expanding population is self-evident. A method for increasing the quantity and/or quality of animal protein supplies while maintaining ordinary feed requirements would facilitate delivery of required food supplies.

In light of the foregoing summary of some demands and limitations of conventional methods for the production of meat products, an improved method for quantative and/or qualitative improvement in animal yields is highly desirable. An object of this invention is to provide new and useful compounds and methods of use for increasing the growth rate, enhancing the lean meat deposition, and/or improving the lean meat to fat ratio in farm and domestic animals. This object is manifest in the following description and particularly delineated in the appended claims.

It has been unexpectedly discovered that oral or parenteral administration of selected 3-amino-4-hydroxy(or alkoxy)phenethanolamine derivatives not only will increase the growth rates of certain warm-blooded animals but also will increase lean meat deposition and improve the lean meat to fat ratio in the bodies of these animals. In this disclosure, the term "lean meat" is used interchangeably with the amount of muscle or protein present in referenced animals. The above-mentioned effects are achieved by oral or parenteral administration to appropriate animals of an effective amount of a compound represented by the following structural formula:

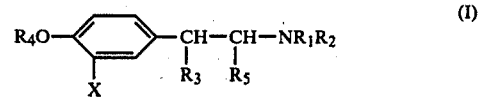
(I)

wherein, $R_1$ is hydrogen or $C_1$–$C_4$ alkyl; $R_2$ is hydrogen, $C_1$–$C_4$ alkyl, cycloalkyl $C_3$–$C_5$, benzyl, phenethyl, α-methylphenethyl or α,α-dimethylphenethyl; $R_3$ is OH, $OR_6$ or $SR_7$; $R_4$ is hydrogen, $C_1$–$C_4$ alkyl, benzyl or $C_2$–$C_5$ alkanoyl; $R_5$ is hydrogen, methyl or ethyl; $R_6$ is $C_1$–$C_6$ alkyl, benzyl, phenyl or allyl; $R_7$ is hydrogen, $C_1$–$C_6$ alkyl, benzyl, phenyl or allyl; X is $NHSO_2R_8$, $N(SO_2R_8)_2$, $N(R_1)_2$, $NHCOR_1$, $NH-CO-N(R_1)_2$, $NSO_2N(R_1)_2$, $NHCOOR_9$, or NHCOO-benzyl; $R_8$ is $C_1$–$C_4$ alkyl; $R_9$ is $C_1$–$C_5$ alkyl; with the provisos that when $R_2$ is cycloalkyl $C_3$–$C_5$, benzyl, phenethyl, α-methylphenethyl or α,α-dimethylphenethyl, $R_1$ of $NR_1R_2$ is hydrogen; and when $R_3$ is $OR_6$ or $SR_7$, X is only $NHSO_2R_7$; and further that the $R_1$ group in $(R_1)_2$ may or may not be identical substituents; and the optically active isomers and pharmacologically acceptable acid addition and metal salts thereof.

A preferred group of compounds of this invention, as depicted by formula I above, are those wherein $R_4$ is hydrogen; $R_3$ is OH; $R_5$ is hydrogen; $R_1$ is hydrogen or $C_1$–$C_4$ alkyl; $R_2$ is hydrogen, $C_1$–$C_4$ alkyl, α,α-dimethylphenethyl or α-methylphenethyl; X is $NHSO_2CH_3$, $N(R_1)_2$, $NHCOR_1$, $NH-CO-N(R_1)_2$, $NSO_2N(R_1)_2$ or $NHCOOR_9$, where $R_9$ is $C_1$–$C_5$ alkyl; with the provisos that when $R_2$ is α-methylphenethyl or α,α-dimethylphenethyl, $R_1$ in $NR_1R_2$ is hydrogen; and further that both $R_1$'s in $(R_1)_2$ may be the same or different substituents; and the optically active isomers and pharmacologically acceptable acid addition and metal salts thereof.

A still more preferred group of compounds of the present invention have the structure depicted by Formula II:

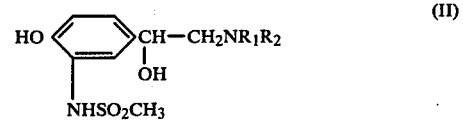
(II)

wherein $R_1$ is hydrogen or $C_1$–$C_4$ alkyl; $R_2$ is $C_1$–$C_4$ alkyl or α,α-dimethylphenethyl; with the proviso that when $R_2$ is α,α-dimethylphenethyl, $R_1$ of $NR_1R_2$ is hydrogen; and the optically active isomers and pharmacologically acceptable acid addition and metal salts thereof.

Among the pharmacologically acceptable acid addition salts useful in the present invention are the hydrochloride, sulfate, phosphate, gluconate, succinate, propionate, oleate, linoleate, linolenate, fumarate and abiate salts.

Novel compounds of the present invention are depicted by the structure shown as Formula III below:

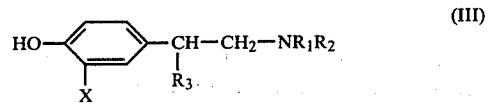
(III)

wherein X is $NHSO_2R_8$ or $N(SO_2R_8)_2$; $R_1$ is hydrogen or $C_1$–$C_4$ alkyl; $R_2$ is hydrogen, $C_1$–$C_4$ alkyl, benzyl, phenethyl, α-methylphenethyl or α,α-dimethylphenethyl; $R_3$ is $OR_6$ or $SR_7$; $R_6$ is $C_1$–$C_4$ alkyl, benzyl, phenyl or allyl; $R_7$ is hydrogen, $C_1$–$C_6$ alkyl, benzyl, phenyl or allyl; $R_8$ is $C_1$–$C_4$ alkyl; with the provisos that when $R_2$ is benzyl, phenethyl, α-methylphenethyl or α,α-dimethylphenethyl, $R_1$ of $NR_1R_2$ is hydrogen; and when X is $N(SO_2R_8)_2$, $R_3$ is OH; and the optionally active isomers and pharmacologically acceptable acid addition and metal salts thereof.

A preferred group of these novel formula III compounds are those wherein $R_3$ is $OR_6$ and $R_1$, $R_2$, $R_6$, $R_8$, and X are as described above for formula III compounds.

Another preferred group of these novel formula III compounds are those wherein $R_3$ is $SR_7$ and $R_1$, $R_2$, $R_7$, $R_8$, and X are as described above for formula III compounds.

Advantageously, the compounds of this invention as delineated by formulas I, II, and III above, generally can be prepared by one or more of the synthetic routes described in the above-identified publication and graphically illustrated below.

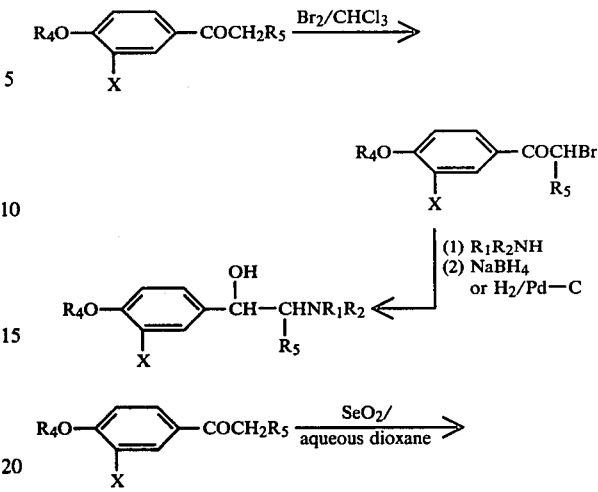

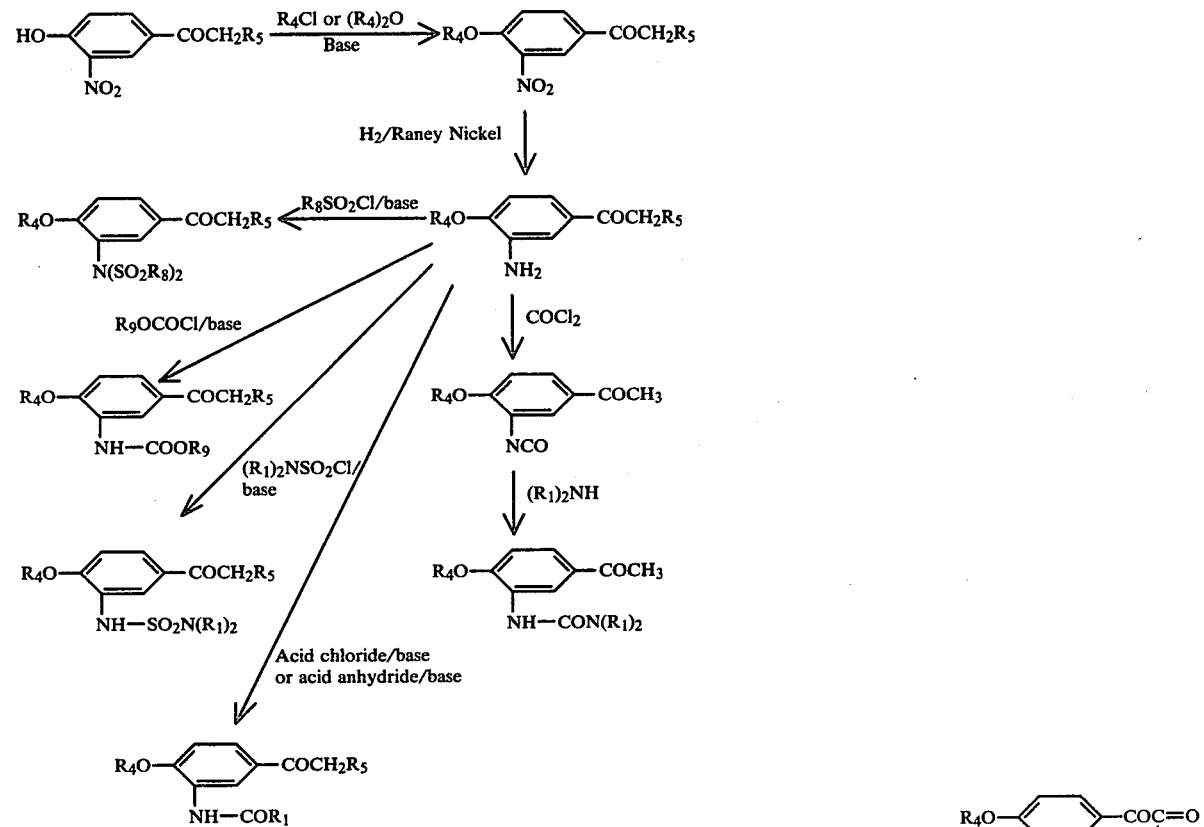

In the above reactions, $R_1$ in the function $(R_1)_2$ may represent the same or different substitutents selected from hydrogen and $C_1$–$C_4$ alkyl and $R_4$ is $C_2$–$C_5$ acyl.

The above-illustrated acetophenone compounds may be converted by the reactions, graphically illustrated below, to compounds of the invention having the formula I structure in which $R_3$ is OH, $R_1$ is hydrogen and X, $R_2$, $R_4$, and $R_5$ are as described for formula I compounds depicted above.

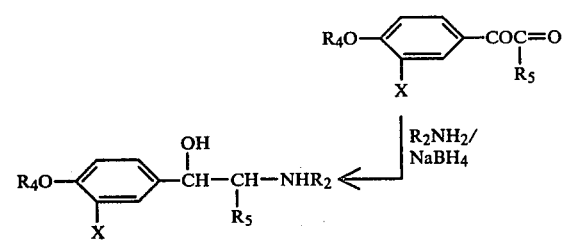

In the above reaction, X, $R_1$, $R_2$, $R_4$, and $R_5$ are as defined with respect to formula I Additionally, the novel 2'hydroxy-5'-[1-alkoxy-2-(alkyl-, dialkyl- or aralkylamino)ethyl]alkanesulfonanilides of this invention can be prepared by the following steps:

(1) reacting a 2'-hydroxy-5'-[1-hydroxy-2-(alkylamino)ethyl]alkanesulfonanilide or the dialkylamino or aralkylamino derivative thereof, with an equivalent amount or slight excess of thionyl chloride to obtain the 2'-hydroxy-5'-[1-chloro-2-(alkyl-, dialkyl- or aralkylamino)ethyl]alkanesulfonanilide hydrochloride;

(2) converting the above-formed alkanesulfonanilide hydrochloride salt to the 2'-hydroxy-5'-[1alkoxy-2-(alkyl-, dialkyl- or aralkylamino)ethyl]alkanesulfonanilide hydrochloride by reacting the hydrochloride salt with the appropriate $C_1$-$C_6$ alcohol at temperature between about 0° to 150° C.; and (3) when a free base of an above-named hydrochloride-salt compound is desired, it is obtained by neutralization of the hydrochloride salt with a suitable aqueous base (i.e., sodium hydroxide, potassium hydroxide etc.).

The 2'-hydroxy-5'-[1-alkoxy-2-(alkyl-, dialkyl- or aralkylamino)ethyl]alkanesulfonanilide derivatives and salts as well as 2'-hydroxy-5'-[1-benzyloxy-2-(alkyl-, dialkyl- or aralkylamino)ethyl]alkanesulfonanilide derivatives and salts are readily prepared by the above-described procedures and further illustrated in the following equations:

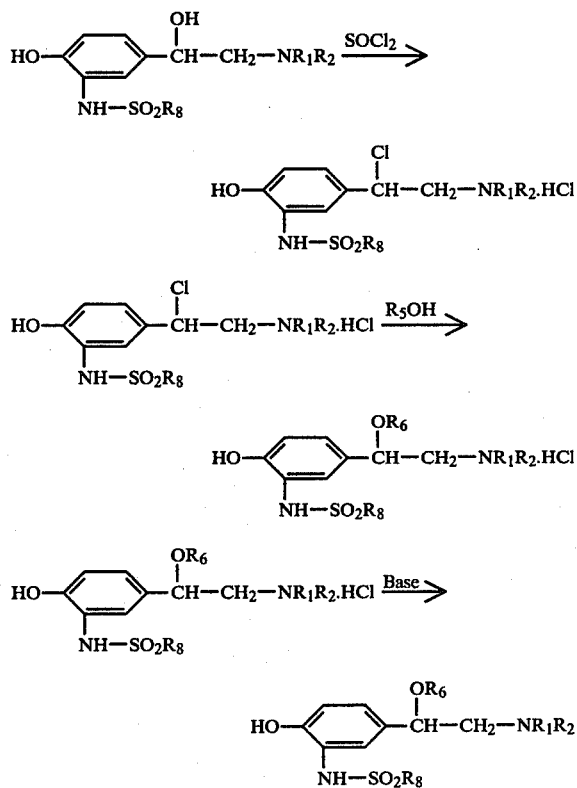

wherein $R_1$ is hydrogen or $C_1$-$C_4$ alkyl; $R_2$ is hydrogen, $C_1$-$C_4$ alkyl, benzyl, phenethyl, α-methylphenethyl or α,α-dimethylphenethyl; $R_8$ is $C_1$-$C_4$ alkyl and $R_6$ is $C_1$-$C_6$ alkyl, benzyl, phenyl or allyl; with the condition that when $R_2$ is benzyl, phenethyl, α-methylphenethyl or α,α-dimethylphenethyl, $R_1$ of $NR_1R_2$ is hydrogen.

The 2'-hydroxy-5'-[1-phenoxy-2-(alkyl-, dialkyl- or aralkylamino)ethyl]alkanesulfonanilide compounds can be prepared by reacting an appropriate 2'-hydroxy-5'-[1-chloro-2-(alkyl-, dialkyl- or aralkylamino)ethyl]alkanesulfonanilide compounds with an excess amount (i.e., preferably 10 to 15 equivalents) of an alkali metal phenoxide in the presence of an aprotic solvent (i.e., tetrahydrofuran, ether, toluene, benzene, etc.). This reaction is carried out at a temperature between about −5° and +10° C. under a blanket of an inert gas.

The 2'-hydroxy-5'-[1-alkyl, benzyl-, or allylthio)-2-(alkyl-, dialkyl-, or aralkylamino)ethyl]alkanesulfonanilide compounds of the invention can be prepared by reacting an appropriate 2'-hydroxy-5'-[1-chloro-2-(alkyl-, dialkyl-, or aralkylamino)ethyl]alkanesulfonanilide hydrochloride with an equimolar or excess amount of an alkyl, benzyl or allylmercaptan (i.e., $R_6SH$).

This reaction is illustrated by the following equation:

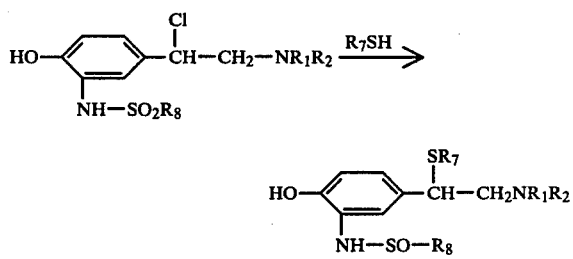

wherein $R_1$ is hydrogen or $C_1$-$C_4$ alkyl, $R_2$ is hydrogen, $C_1$-$C_4$ alkyl, benzyl, phenethyl, α-methylphenethyl or α,α-dimethylphenethyl; $R_8$ is $C_1$-$C_4$ alkyl; $R_7$ is hydrogen, $C_1$-$C_6$ alkyl, benzyl, or allyl. This reaction is generally conducted in the presence of an aprotic solvent (i.e., a chlorinated hydrocarbon such as ether or other similar material) at a temperature ranging from −5° to +50° C. under a blanket of an inert gas.

The 2'-hydroxy-5'-[1-phenylthio-2-(alkyl-, dialkyl-, or aralkylamino)ethyl]alkanesulfonanilides can be prepared by reacting an appropriate 2'-hydroxy-5'-[1-chloro-2-(alkyl-, dialkyl-, or aralkylamino)ethyl]alkanesulfonanilide compound with an excess amount of an alkali metal thiophenoxide (i.e., sodium or potassium thiophenoxide) in an aprotic solvent (i.e., tetrahydrofuran, benzene, toluene or ether) at a temperature ranging from about −5° to +10° C. under a blanket of an inert gas.

The formula I compounds of this invention can generally be administered either orally or parenterally to domestic or farm animals with resultant increases in growth rates and enhancement of the lean meat to fat ratio in these animals. In actual practice, the formula I compounds may be directly mixed with animal feeds or prepared in the form of an animal-feed premix, concentrate, or supplement which can be blended with or applied as a top dressing to animal feeds. Regardless of the procedure selected, the active compound should be present at levels from about 0.05 to 500 ppm and preferably 0.1 to 100 ppm in the feed.

Animal-feed premixes, supplements or concentrates can be prepared by mixing on a weight basis about 0.5 to 50% of a suitable formula I compound with about 50 to 99.5% of an edible diluent. Diluents suitable for use in the manufacture of animal-feed supplements, concentrates, and premixes include the following: corn meal, soybean meal, bone meal, alfalfa meal, cottonseed oil meal, urea, molasses, and other similar materials. Use of the diluents in feed supplements, concentrates, and premixes improves uniformity of distribution of the active ingredient in the finished feed.

Feeds for swine, cattle, sheep, and goats preferably contain about 0.05 to 400 grams of active ingredient per ton of feed with an optimum level of about 0.25 to 100 grams per ton. Preferred poultry and domestic-pet feeds range from about 0.05 to 400 grams and most preferably 0.2 to 100 grams of active ingredient per ton of feed.

When parenteral administration is desired, formula I compounds may be formulated as pastes or pellets and adminstered to the animals by subcutaneous injection. This procedure involves injection of a formula I compound in an amount sufficient to provide the animal with 0.001 to 100 mg/kg of body weight/day of the active compound. The preferred dosage for swine, cattle, sheep, and goats ranges from about 0.0001 to 50 mg/day/kg of body weight of the active formula I compound. The preferred dosage for poultry and domestic pets ranges from about 0.001 to 10 mg/day/kg of body weight.

Paste formulations suitable for subcutaneous injection can be prepared by dispersing formula I compound in a pharmacologically acceptable oil (i.e., peanut oil, corn oil, seasame oil, etc.). Pellets for subcutaneous injection can be prepared by mixing a formula I compound with a suitable diluent (i.e., carbowax, carnauba wax, etc.). A lubricant (i.e., magnesium or calcium stearate) can be added to improve the pelleting process.

In order to obtain the drug dosage levels necessary to achieve desired results (i.e., increase in growth rates and improvement in lean meat to fat rates), it may be necessary to administer multiple pellets. Also, implants may be made periodically during treatment periods in order to maintain proper animal drug levels.

In addition to improved growth rates and enhanced lean meat to fat ratios, administration of formula I compounds to meat-producing animals frequently results in enhanced efficiency of feed utilization thereby. With the use of materials and methods revealed in the present invention, producers can market superior quality meat animals in a short period of time while incurring minimum feed costs.

The following non-limiting examples further serve to illustrate the invention.

EXAMPLE 1

Preparation of 2'-hydroxy-5'-[1-chloro-2-(isopropylamino)ethyl]methanesulfonanilide hydrochloride A 1-g sample of 2'-hydroxy-5'-[1-hydroxy-2-(isopropylamino)ethyl]methanesulfonanilide is added to 2 mL of ice-cold thionyl chloride. The mixture is then stirred at ambient temperature until the reaction is completed. Excess thionyl chloride is removed in vacuo, and the residue is washed with ethyl ether thus yielding the product compound.

The compound 2'-hydroxy-5'-[1-chloro-2-(isopropylamino)ethyl]methanesulfonanilide hydrochloride can also be prepared by heating 1 g of 2'-hydroxy-5'-[1-hydroxy-2-(isopropylamino)ethyl]methanesulfonanilide in 10 mL of dry acetonitrile or dry dimethoxyethane containing 2 mL of thionyl chloride at reflux temperature for 10 minutes following the procedure described in the *Journal of Medicinal Chemistry*, 19, 632 (1976).

EXAMPLE 2

Preparation of 2'-hydroxy-5'-[1-ethoxy-2-(isopropylamino)ethyl]methanesulfonanilide hydrochloride A 1-g sample of 2'-hydroxy-5'-[1-chloro-2-isopropylamino)ethyl]methanesulfonanilide hydrochloride is added to 10 mL of absolute ethanol and heated at reflux for 30 minutes. The mixture is evaporated to dryness, and the residue is washed with ethyl ether thus yielding the product compound. The same procedure is used to prepare 2'-hydroxy-5'-[1-isopropoxy-2-(isopropylamino)ethyl]methanesulfonanilide hydrochloride, m.p. 121-123, by substituting isopropanol for ethanol in the above reaction.

Neutralization of the 2'-hydroxy'5'-[1-ethoxy-2-(isopropylamino)ethyl]methanesulfonanilide hydrochloride salt with aqueous sodium hydroxide yields the free base of this compound which can be separated from the aqueous solution and readily converted to other acid salts by tritration.

EXAMPLE 3

Preparation of chloro intermediates

Several chloro intermediates can be prepared by the method of Example 1 as illustrated in the following equation:

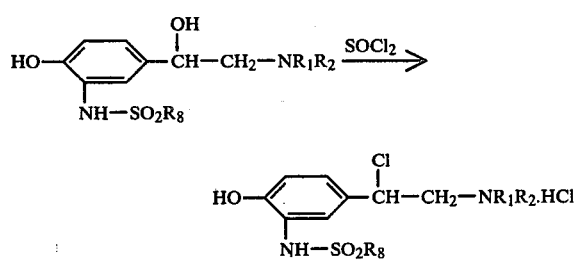

wherein substituents are:

| R₁ | R₂ | R₈ |
| --- | --- | --- |
| H | t-butyl | methyl |
| H | n-propyl | methyl |
| H | i-propyl | n-butyl |
| methyl | methyl | methyl |
| H | benzyl | methyl |
| H | t-butyl | n-propyl |
| ethyl | ethyl | methyl |
| H | phenethyl | methyl |
| H | α, α-dimethylphenethyl | methyl |

EXAMPLE 4

Preparation of ethers

Several ethers can be prepared according to the method of Example 2 as illustrated in the following equation:

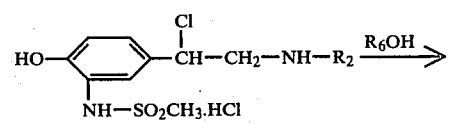

-continued

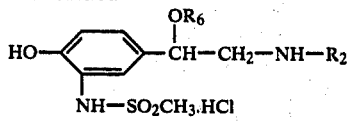

wherein substituents are:

| R$_2$ | R$_6$ | M.P.°C. |
| --- | --- | --- |
| isopropyl | methyl | |
| isopropyl | benzyl | |
| isopropyl | allyl | |
| t-butyl | ethyl | |
| isopropyl | isopropyl | 121–123 |
| phenethyl | ethyl | |
| α, α-dimethylphenethyl | methyl | |
| α, α-dimethylphenethyl | ethyl | |
| isopropyl | n-butyl | |
| isopropyl | n-hexyl | |
| α, α-dimethylphenethyl | isopropyl | 210–212 |

EXAMPLE 5

Preparation of 2'-hydroxy-5'-[phenoxy-2-(isopropylamino)ethyl]methanesulfonanilide A 3.25 g sample of 2'-hydroxy-5'-[1-chloro-2-(isopropylamino)ethyl]methanesulfonanilide hydrochloride is slowly added to 45 g of sodium phenoxide in 150 mL of dry tetrahydrofuran at 0° to 5° C. under N$_2$ atmosphere. The mixture is stirred for 24 hours at ambient temperature and then poured on ice whereafter the crude product compound is separated.

EXAMPLE 6

Preparation of 2'-hydroxy-5'-[1-phenylthio-2-(isopropylamino)ethyl]-methanesulfonanilide The compound 2'-hydroxy-5'-[1-phenylthio-2-(isopropylamino)ethyl]methanesulfonanilide can be prepared following the method described in Example 5 with the substitution of sodium thiophenoxide for sodium phenoxide.

EXAMPLE 7

Preparation of 2'-hydroxy-5'-[1-methylthio-2-(isopropylamino)ethyl]-methanesulfonanilide A 1-g sample of 2'-hydroxy-5'-[1-chloro-2-(isopropylamino)ethyl]methanesulfonanilide hydrochloride is slowly added to 5 mL of methylmercaptan in 25 mL of ethylene dichloride at 0° to −10° C. under N$_2$ atmosphere. This mixture is first stirred several hours at ice-bath temperature and then stirred at ambient temperature for 24 hours. The mixture is filtered. The filter cake is washed with ethylene dichloride, added to water, and basified with 10% NaOH solution to pH 10 in an ice bath. The aqueous mixture is extracted several times with methylene chloride. The combined extracts are dried over MgSO$_4$ and evaporated to dryness thus yielding the crude product compound.

EXAMPLE 8

Several thioethers can be prepared using the method of Example 7 as illustrated in the following equation:

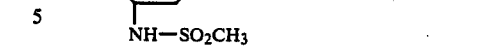

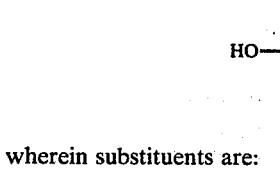

wherein substituents are:

| R$_2$ | R$_7$ |
| --- | --- |
| isopropyl | isopropyl |
| isopropyl | benzyl |
| t-butyl | methyl |
| phenethyl | methyl |
| α, α-dimethylphenyl | methyl |
| isopropyl | ethyl |
| isopropyl | allyl |

Use of NaSH in place of R$_7$SH without further basification yields:

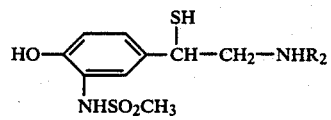

EXAMPLE 9

2'-Acetoxy-5'-[2-(isopropylamino)-1-hydroxyethyl]aniline hydrochloride

A mixture containing 36.2 g (0.2 mole) of 4'-hydroxy-3'-nitroacetophenone, 15.7 g of acetyl chloride, 22 mL of 50% KOH solution, 200 mL of H$_2$O and 300 mL of 95% ethanol is stirred and heated to reflux for 18 hours. The mixture is evaporated to remove ethanol, and the aqueous mixture is extracted with CHCl$_3$ to solubilize the product. The CHCl$_3$ extract is evaporated to dryness to afford 4'-acetoxy-3'-nitroacetophenone, which is brominated with an equimolar quantity of Br$_2$ in CHCl$_3$ (100 mL) to afford 2-bromo-4'-acetoxy-3-nitroacetophenone. This phenacyl bromide is then reacted in 100 mL of ethanol with 2 equivalents of isopropylamine to afford 4'-acetoxy-3'-nitro-2-isopropylaminoacetophenone, which isolated as the hydrochloride by the procedure reported by Larson et al. in *Journal of Medicinal Chemistry*, 10, 467 (1967) for a related compound. This ketoamine is then hydrogenated in 90% aqueous ethanol with 0.5 g of 10% Pd-C/3.5 kg/cm$^2$ H$_2$ pressure in a Parr hydrogenator until the uptake of H$_2$ is completed. The mixture is filtered, and the filtrate is evaporated to dryness to afford the crude title compound.

Similarly, substitution of pivaloyl chloride, butyryl chloride, propionyl chloride, isobutyryl chloride, and valeryl chloride in place of acetyl chloride in the above sequence affords the corresponding 2'-pivaloyoxy-, 2'-butyryloxy-2'-propionyloxy-, 2'-isobutyryloxy-, and 2'-valeryloxy-5'-[2-(isopropylamino)-1-hydroxyethyl]aniline hydrochlorides. Similarly, substitution of the isopropylamine by t-butylamine, 2-butylamine, ethylamine, n-propylamine, cyclopentylamine and α,α-dimethylphenethylamine affords the following compounds:

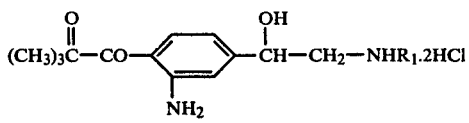

EXAMPLE 10

2'-Pivaloyloxy-5-[1-hydroxy-2-(α,α-dimethylphenethylamino)ethyl]methanesulfonanilide 2'-Pivaloyloxy-3'-nitroacetophenone (10 g), which is prepared by the method described in Example 9, in 200 mL of MeOH is reduced in a Parr hydrogenator with 0.2 g of PtO₂. The mixture is filtered, and the solvent is removed to afford crude 2'-pivaloyoxy-3'-aminoacetophenone. This material is stirred in 75 mL of pyridine and 4.32 g of methanesulfonyl chloride is added dropwise at 25° C. After three hours, the mixture is poured into an ice water mixture, and the precipitate is collected and washed with H₂O, dilute HCl and H₂O successively to afford 2'-pivaloyloxy-5'-acetylmethanesulfonanilide. This material is then brominated by the procedure of Example 9 to afford 2'-pivaloyloxy-5'-(2-bromoacetyl)methanesulfonanilide, which is then reacted with isopropylamine according to the procedure of Example 9 to afford 2'-pivaloyloxy-5'-(2-isopropylaminoacetyl)methanesulfonanilide hydrochloride. This intermediate is then reduced by the procedure of Example 9 to yield 2'-pivaloyloxy-5'-[(2-isopropylamino)-1-hydroxyethyl]methanesulfonanilide hydrochloride.

Similarly, the following compounds are prepared by the above sequence with or without different acyl chlorides (R₄Cl) for pivaloyl chloride and with or without substitution of R₁R₂NH for isopropylamine.

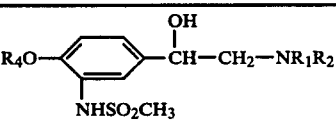

| R₄ | R₁ | R₂ |
|---|---|---|
| CH₃CO | H | isopropyl |
| CH₃CO | H | α,α-dimethylphenethyl |
| CH₃CO | H | t-butyl |
| C₂H₅CO | H | isopropyl |
| C₂H₅CO | H | α,α-dimethylphenethyl |
| C₂H₅CO | H | t-butyl |
| n-C₃H₇CO | H | isopropyl |
| n-C₃H₇CO | H | t-butyl |
| n-C₃H₇CO | H | α,α-dimethylphenethyl |
| i-C₃H₇CO | H | isopropyl |
| i-C₃H₇CO | H | α,α-dimethylphenethyl |
| i-C₃H₇CO | H | t-butyl |
| pivaloyl | H | t-butyl |
| pivaloyl | H | α,α-dimethylphenethyl |
| pivaloyl | H | cyclopentyl |
| pivaloyl | methyl | methyl |

EXAMPLE 11

N-{2-Hydroxy-5-[1-hydroxy-2-(isopropylamino)ethyl]-phenyl}dimethanesulfonamide

In 250 mL of CH₂Cl₂ containing 26 mL of triethylamine, 20 g of 3'-amino-4'-benzyloxyacetophenone is stirred at 10° C. and 19 g of methanesulfonyl chloride is added gradually. The mixture is then stirred at room temperature for 24 hours and extracted with 10% aqueous NaOH solution. The CH₂Cl₂ solution is further washed with H₂O, dried over MgSO₄, and evaporated in vacuo until crystallization begins to occur. The dimethanesulfonamide derivative (A) is then collected. In 100 mL of dioxane containing 7 mL of H₂O, and 7 mL of H₂O, and 8.2 g of selenium dioxide, compound A is added gradually at 70° C. Heating is continued for an overnight period, and the mixture is heated at reflux for an hour. The mixture is decolorized with activated carbon, filtered, and evaporated to dryness in vacuo. The residual oil is mixed with 500 mL of CH₂Cl₂ and washed twice with 100 mL of H₂O. The CH₂Cl₂ solution is dried over MgSO₄ and evaporated to dryness to afford the crude glyoxal, which is further dissolved in 100 mL of CH₂Cl₂. A half of this solution is stirred, and 3.2 mL of isopropyl amine is gradually added. After one hour, the mixture is evaporated to dryness; the residue is triturated with ether and filtered. This solid is stirred in 250 mL of ethanol at 15° C. and 2.4 g of NaBH₄ is added in one portion. The mixture is stirred at room temperature overnight and evaporated to dryness. The residual solid is heated in 200 mL of boiling CH₂Cl₂ and filtered. This washing procedure is repeated twice. The remaining residue is partially dissolved in 30 mL of CH₂Cl₂, and the mixture is washed with H₂O (3×200 mL). The CH₂Cl₂ solutions are combined, washed with H₂O (3×300 mL), dried over MgSO₄, and evaporated to dryness to afford a yellow oil. This oil is triturated with Et₂O to afford 5.5 g of pale-yellow solid (B) after filtration. A 5-gram sample of B is added to 200 mL of MeOH containing 1 g of 5% Pd-C and hydrogenated at 50-45 p.s.i.g. until uptake of H₂ is completed. The mixture is filtered; the catalyst is washed with 50 mL of MeOH, and the methanol solutions are evaporated to dryness to afford the crude title compound, which is washed with ether; m.p. 174° C.

The following compounds are prepared in the above manner with or without substitution of methanesulfonyl chloride with the appropriate R₈SO₂Cl and with or without substitution of isopropylamine with R₂NH₂.

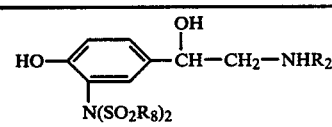

| R₈ | R₂ |
|---|---|
| C₂H₅ | isopropyl |
| methyl | t-butyl |
| methyl | α,α-dimethylphenethyl |
| isopropyl | isopropyl |
| n-butyl | isopropyl |
| n-butyl | t-butyl |
| n-butyl | α,α-dimethylphenethyl |
| isopropyl | t-butyl |
| isopropyl | α,α-dimethylphenethyl |
| methyl | cyclopentyl |
| methyl | α-methylphenethyl |
| methyl | ethyl |

EXAMPLE 12

Evaluation of test compounds for increasing the growth rate of animals and enhancing the lean meat to fat ratio thereof by reducing fat deposition in said animals and increasing the lean meat thereof CIF female mice from Carworth Farms are received when they are six weeks old. They are housed ten to a cage in air-conditioned rooms (22° C. to 25° C.) with automatic diurnal illumination (14 hours light and 10 hours dark). Compounds of the invention are added to a basic diet of Purina Laboratory Chow which is supplied ad libitum and contains the following ingredients:

TABLE I

| Description of Diet | |
|---|---|
| Guaranteed Analysis | % |
| Crude protein not less than | 23.0 |
| Crude fat not less than | 4.5 |
| Crude Fiber not more than | 6.0 |
| Ash not more than | 9.0 |

INGREDIENTS

Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewer's dried yeast, thiamin, niacin, vitamin A supplement, D-activated plant sterol, vitamin E supplement, calcium carbonate, dicalcium phosphate, iodized salt, ferric ammonium citrate, iron oxide, manganous oxide, cobalt carbonate, copper oxide, zinc oxide. Water is also allowed ad libitum.

Various experimental treatments are randomly assigned to mice cages. Each treatment is tested with three replicates, i.e., in three cages of ten mice each. There are ten control cages each of which contains ten mice. Drugs are mixed in the diet at the dosage level indicated. Feed and water are offered ad libitum over a 12-day test period. Feed spilled is collected during the test period. At the end of the experiment the collected feed is weighed and the mean feed consumption per cage of ten mice is determined for each treatment. The mice are weighed as a group of ten and the weight gain is determined. The mice are sacrificed by cervical dislocation. The right uterine fat pad of each mouse is removed. The fat pads for each cage of ten mice are weighed as a unit.

A correlation between the reduction in fat pad weights of treated animals and reduction in total body fat of treated animals has been previously established. This relationship was established using several treatment groups in which the total body fat of treated animals was determined and found to correlate closely with reduction in fat pad weights of animals receiving the same treatment.

Results of representative experiments are presented in Table II. These data indicate that compounds of the invention cause increases in growth as measured by weight gain and concomitant decreases in body fat of experimental animals.

TABLE II

Evaluation of test compounds for growth enhancement and reduction of fat pad weight in mice

| Compound | Level in diet (ppm) | Gain (g) | % ± Control | Fat pad wt % ± control |
|---|---|---|---|---|
| HO—⟨phenyl, NHSO$_2$CH$_3$⟩—CH(OH)—NH—CH(CH$_3$)$_2$·HCl | 200 | 15.3 | +27.5 | −26.3 |
| | 100 | 17.0 | +41.7 | −24.5 |
| | 50 | 15.5 | +29.2 | −7.1 |
| | 25 | 11.7 | +2.5 | −19.9 |
| | 12 | 12.2 | +1.7 | −12.8 |
| | 6 | 11.7 | +2.5 | −11.3 |
| HO—⟨phenyl, NH$_2$—CO—NH⟩—CH(OH)CH$_2$—NH—C(CH$_3$)$_3$ | 100 | 13.1 | +23.6 | −13.5 |
| HO—⟨phenyl, NHSO$_2$CH$_3$⟩—CH(OH)—CH$_2$—NH—C(CH$_3$)$_2$—CH$_2$—⟨phenyl⟩·HCl | 200 | 17.3 | +44.3 | −51.1 |
| | 100 | 12.9 | +7.5 | −36.9 |
| | 50 | 15.5 | +29.2 | −25.5 |
| | 25 | 12.1 | +0.8 | −13.2 |
| | 12 | 13.5 | +12.5 | +4.2 |
| | 6 | 15.1 | +25.8 | −7.0 |
| HO—⟨phenyl, CH$_3$—CO—NH⟩—CH(OH)CH$_2$—NH—C(CH$_3$)$_3$ | 50 | 18.7 | +77.4 | −5.1 |
| ⟨phenyl⟩—CH$_2$—O—⟨phenyl, NH—CO—OCH$_3$⟩—CH(OH)CH$_2$—NH—C(CH$_3$)$_3$ | 200 | 21.4 | +46.6 | −7.1 |
| HO—⟨phenyl, NH—CO—OCH$_3$⟩—CH(OH)CH$_2$—NH—C(CH$_3$)$_3$ | 200 | 24.5 | +67.8 | +0.6 |
| | 50 | 22.9 | +56.8 | +1.8 |

TABLE II-continued
Evaluation of test compounds for growth enhancement and reduction of fat pad weight in mice

| Compound | Level in diet (ppm) | Gain (g) | % ± Control | Fat pad wt % ± control |
|---|---|---|---|---|
| HO—C₆H₃(NHSO₂CH₃)—CHCH₂—NH—CH(CH₃)₂·HCl, O—CH(CH₃)₂ | 200 | 18.4 | +41.5 | +3.8 |
|  | 50 | 16.9 | +30.0 | −2.4 |
| HO—C₆H₃(NHSO₂CH₃)—CHCH₂—NH—C(CH₃)₂—CH₂—C₆H₅·HCl, O—CH(CH₃)₂ | 50 | 13.6 | +3.8 | −7.0 |
| HO—C₆H₃(N(SO₂CH₃)₂)—CHCH₂—NH—CH(CH₃)₂, OH | 200 | 15.0 | +41.5 | +4.7 |
| HO—C₆H₃(N(SO₂CH₃)₂)—CHCH₂—NH—C(CH₃)₂—CH₂—C₆H₅, OH | 200 | 17.5 | +65.1 | −15.5 |
| HO—C₆H₃(NHSO₂N(CH₃)₂)—CH(OH)—CH₂—NHCH(CH₃)₂·½ HOOC—C=C—H / H—C—COOH (m.p. 198–200° C.) | | | | |
| HO—C₆H₃(NHSO₂N(CH₃)₂)—CH(OH)—CH₂—NHC(CH₃)₂CH₂—C₆H₅·HCl | | | | |
| HO—C₆H₃(NHSO₂CH₃)—CH(OH)—CH₂—NHC(CH₃)₃·HCl (m.p. 236–237° C.) | | | | |
| HO—C₆H₃(NH₂)—CH(OH)—CH₂—NHCH(CH₃)₂·2HCl | | | | |
| HO—C₆H₃(NH₂)—CH(OH)—CH₂—NHC(CH₃)₃·2HCl | | | | |

I claim:

1. A compound having the structural formula:

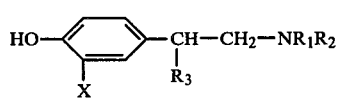

wherein X is $N(SO_2R_8)_2$, and $R_8$ is $C_1$–$C_4$ alkyl; $R_1$ is hydrogen or $C_1$–$C_4$ alkyl; $R_2$ is hydrogen, $C_1$–$C_4$ alkyl, benzyl, phenethyl, α-methylphenethyl, or α,α-dimethylphenethyl; $R_3$ is OH; with the provisos that when $R_2$ is benzyl, phenethyl, α-methylphenethyl or α,α-dimethylphenethyl, $R_1$ of $NR_1R_2$ is hydrogen; and the optically active isomers, and the pharmacologically acceptable acid addition and metal salts thereof.

2. A compound according to claim 1, N-{2-hydroxy-5-[1-hydroxy-2-(isopropylamino)ethyl]phenyl}dimethanesulfonamide and the optical isomers and acid addition salts thereof.

3. A compound according to claim 1, [N,[5-[2-[(α,α-dimethylphenethyl)amino]-1-hydroxyethyl]-2'-hydroxyphenethyl]dimethanesulfonamide] N-[5-[2-[(α,α-dimethylphenethyl)amino]-1-hydroxyethyl]-2-hydroxyphenyl]dimethanesulfonamide and the optical isomers and acid addition salts thereof.

* * * * *